US009097602B2

(12) United States Patent
DeTeresa et al.

(10) Patent No.: US 9,097,602 B2
(45) Date of Patent: Aug. 4, 2015

(54) SYSTEMS AND METHODS FOR DETERMINING STRENGTH OF CYLINDRICAL STRUCTURES BY INTERNAL PRESSURE LOADING

(71) Applicant: Lawrence Livermore National Security, LLC, Livermore, CA (US)

(72) Inventors: Steven John DeTeresa, Livermore, CA (US); Scott Eric Groves, Brentwood, CA (US); Roberto Joseph Sanchez, Pleasanton, CA (US); William Andrew Andrade, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 185 days.

(21) Appl. No.: 13/748,443

(22) Filed: Jan. 23, 2013

(65) Prior Publication Data

US 2014/0202256 A1    Jul. 24, 2014

(51) Int. Cl.
*G01N 3/12* (2006.01)
*G01M 5/00* (2006.01)
(Continued)

(52) U.S. Cl.
CPC ............... *G01M 5/005* (2013.01); *G01N 3/12* (2013.01); *E21B 33/128* (2013.01); *E21B 43/105* (2013.01); *G01N 2203/0266* (2013.01); *G01N 2203/0274* (2013.01)

(58) Field of Classification Search
CPC ....... E21B 33/128; E21B 43/105; G01N 3/12; G01N 2203/0266; G01N 2203/0274
USPC ........... 73/788, 799, 794, 795, 832, 831, 826, 73/838
See application file for complete search history.

(56) References Cited

U.S. PATENT DOCUMENTS 4,358,961 A  * 11/1982 Woods, Jr. .................... 73/827
4,867,205 A     9/1989 Bournazel et al.
(Continued)

FOREIGN PATENT DOCUMENTS

EP     0147288 A2   7/1985
EP     0972980 A2   1/2000
(Continued)

OTHER PUBLICATIONS

Aleong et al., "Effect of Winding Tension and Cure Schedule on Residual Stresses in Radially-Thick Fiber Composite Rings," Polymer Engineering & Science, vol. 31, Issue 18, Sep. 1991, pp. 1344-1350.
(Continued)

*Primary Examiner* — Lisa Caputo
*Assistant Examiner* — Jonathan Dunlap
(74) *Attorney, Agent, or Firm* — Zilka Kotab, PC

(57) ABSTRACT

In one embodiment, an apparatus, includes: a mandrel; an expansion cylinder, comprising: opposite first and second ends; an inner circumferential surface extending between the ends and characterized by an inner diameter, the inner circumferential surface defining a hollow cavity; an outer circumferential surface extending between the ends and characterized by an outer diameter that is greater than the inner diameter; and a plurality of slots extending from the inner circumferential surface to the outer circumferential surface and latitudinally oriented between the ends; and one or more base plates configured to engage one of the ends of the expansion cylinder. In another embodiment, a method includes: arranging an expansion cylinder inside a test cylinder; arranging a mandrel inside the expansion cylinder; applying a force to the mandrel for exerting a radial force on the expansion cylinder; and detecting one or more indicia of structural failure of the test cylinder.

19 Claims, 7 Drawing Sheets

(51) Int. Cl.
  *E21B 43/10* (2006.01)
  *E21B 33/128* (2006.01)

(56) References Cited

U.S. PATENT DOCUMENTS

| | | | |
|---|---|---|---|
| 5,520,422 | A | 5/1996 | Friedrich et al. |
| 5,622,098 | A | 4/1997 | Piper |
| 6,206,111 | B1 | 3/2001 | Nistor |
| 6,491,882 | B1 | 12/2002 | Van Den Berg et al. |
| 7,152,487 | B2 * | 12/2006 | Rufin ............................. 73/826 |
| 7,503,594 | B2 | 3/2009 | Peacock et al. |
| 8,342,034 | B2 * | 1/2013 | Kane ............................... 73/826 |
| 2005/0052025 | A1 | 3/2005 | Peacock et al. |
| 2006/0075827 | A1 * | 4/2006 | Rufin ............................. 73/826 |
| 2009/0166921 | A1 | 7/2009 | Jacob et al. |
| 2009/0286078 | A1 | 11/2009 | Lee et al. |
| 2009/0286904 | A1 | 11/2009 | Lee et al. |
| 2011/0132100 | A1 * | 6/2011 | Kane ............................... 73/826 |
| 2012/0181017 | A1 * | 7/2012 | Hart et al. ...................... 166/207 |

FOREIGN PATENT DOCUMENTS

| | | |
|---|---|---|
| EP | 0978677 B1 | 3/2004 |
| JP | 2002295777 A | 10/2002 |
| JP | 5177722 B2 | 4/2013 |
| WO | WO2005105417 A1 | 11/2005 |
| WO | WO2008003767 A1 | 1/2008 |

OTHER PUBLICATIONS

Dong, C., "Development of an Engineering Model for Predicting the Transverse Coefficients of Thermal Expansion of Unidirectional Fiber Reinforced Composites," Journal of Engineering Materials and Technology vol. 131, Issue. 3, May 21, 2009, 7 pages (Abstract Only).

Chun et al., "Behavior of a Unidirectional Metal-Matrix Composite Under Thermomechanical Loading," Journal of Engineering Materials and Technology, Transactions of the ASME, vol. 118, No. 3, 1996, pp. 310-316 (Abstract Only).

Kim et al., "Measurement of Residual Stresses in Thick Composite Cylinders by the Radial-Cut-Cylinder-Bending Method," Composite Structures, vol. 77, 2007, pp. 444-456.

Dvorak et al., "Thick-Walled Composite Cylinders With Optimal Fiber Prestress," Composites Part B: Engineering, vol. 27, Issue 6, 1996, pp. 643-649.

Wang et al., "Prediction of Axial Longitudinal Shear Modulus of Multiphase Fiber Composites," Journal of Beijing University of Aeronautics and Astronautics, vol. 28, No. 3, 2002, pp. 335-338 (English Abstract Included).

Fischer et al., "Experimental Failure Effect Analysis of Composite High-Speed Flywheel Rotors," Composite Materials: Testing and Design, Fourteenth Volume, American Society for Testing and Materials Special Technical Publication, vol. 1436, 2003, pp. 121-131 (Abstract Only).

Xu et al., "Design and Construction of Insulation Configuration for Ultra-High-Temperature Microwave Processing of Ceramics," Journal of the American Ceramic Society, vol. 86, Issue 12, Nov. 2003, pp. 2082-2086.

Gotsis et al., "Progressive Fracture of Fiber Composite Thin Shell Structures Under Internal Pressure and Axial Loads," International Journal of Damage Mechanics, vol. 7, Issue 4, Sep. 1996, pp. 1-18.

Ha et al., "Effects of Winding Angles on Through-Thickness Properties and Residual Strains of Thick Filament Wound Composite Rings," Composites Science and Technology, vol. 65, Issue 1, Jan. 2005, pp. 27-35.

Ha et al., "Effects of Rotor Sizes and Epoxy System on the Process-Induced Residual Strains within Multi-Ring Composite Rotors," Journal of Composite Materials, vol. 38, No. 10, May 2004, pp. 871-885.

Hahn, T. A., "Thermal-Expansion of TiA1+TiB2 Alloys and Model Calculations of Stresses and Expansion of Continuous Fiber Composites," International Journal of Thermophysics, vol. 12, No. 4, 1991, p. 711-722.

Jacquemin et al., "A Closed-Form Solution for the Internal Stresses in Thick Composite Cylinders Induced by Cyclical Environmental Conditions," Composite Structures, vol. 58, 2002, pp. 1-9.

Kim et al., "Continuous Curing and Induced Thermal Stresses of a Thick Filament Wound Composite Cylinder," Journal of Reinforced Plastics and Composites, vol. 20, No. 2, Jan. 2001, pp. 166-180.

Kim et al., "Buckling Analysis of Filament-Wound Thick Composite Cylinder Under Hydrostatic Pressure," International Journal of Precision Engineering and Manufacturing, vol. 11, No. 6, Dec. 2010, pp. 909-913.

Fu et al., "Response of Thick Composite Rings Under Uniform External Pressure," Composite Structures, vol. 31, No. 4, 1995, pp. 325-338.

Li et al., "Simulation of Process-Induced Residual Stresses in Thick Filament Wound Tubes," Fourth Joint Canada-Japan Workshop on Composites, Sep. 2002, pp. 271-282 (Abstract Only).

Powell et al., "Aspects of Residual Thermal Stresses in Continuous-Fiber-Reinforced Ceramic-Matrix Composites," Composites Science and Technology, vol. 47, Issue 4, 1993, pp. 359-367.

Roy et al., "Design of Thick Composite Cylinders," Journal of Pressure Vessel Technology, vol. 110, Issue 3, Aug. 1, 1988, pp. 255-262 (Abstract Only).

Sridharan et al., "On the Buckling and Collapse of Moderately Thick Composite Cylinders Under Hydrostatic Pressure," Composites Part B: Engineering, vol. 28, Issue 5-6, 1997, pp. 583-596.

Swanson et al., "Analysis of a Fiber Composite Cylinder Laminated with an Elastic-Plastic Aluminum Liner under Internal Pressure Loading," Journal of Thermoplastic Composite Materials, vol. 11, No. 5, Sep. 1998, pp. 466-477 (Abstract Only).

Tzeng et al., "A Thermal/Mechanical Model of Axially Loaded Thick-Walled Composite Cylinders," Composites Engineering, vol. 4, No. 2, 1994, pp. 219-232.

Whitney et al., "A Modified Three-Phase Model for Determining the Elastic Constants of a Short Fiber Composite," Journal of Reinforced Plastics and Composites, vol. 16, No. 8, pp. 714-730 (Abstract Only), May 1997.

Statement of Relevance of Non-Translated Foreign Document for JP5177722.

* cited by examiner

SYSTEMS AND METHODS FOR DETERMINING STRENGTH OF CYLINDRICAL STRUCTURES BY INTERNAL PRESSURE LOADING

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to systems and methods for stress-testing materials, and particularly, to systems and methods for determining strength of cylindrical structures by internal pressure loading.

BACKGROUND

It is known that cylindrical structures configured for use in high-stress applications such as energy conservation flywheels, firearm barrels, high-pressure storage, etc. must be constructed from materials having sufficient strength to retain structural integrity under extreme conditions including temperature, pressure, etc. For example, a gun barrel must be sufficiently strong enough to contain the pressure and temperature produced by the explosive discharge reaction when firing a round. Similarly, flywheels must be sufficiently strong enough to retain structural integrity while rotating around a central axis at extremely high speeds to efficiently store kinetic energy for subsequent use.

Therefore, it is critical to have a precise understanding of the structural properties of materials forming a system designed for use in applications involving such extreme conditions. Typically, with specific regard to pressure load capacity, and more specifically internal pressure load capacity, materials such as flywheels are tested by placing the flywheel system in a remote location (e.g. an underground bunker) and observing the effect of increasing stress on the flywheel (e.g. by placing sensors on the flywheel, by recording the test via cinematographic or photographic means, etc.). In particular, a flywheel is conventionally spun around an axis, and the rotational speed is increased until the flywheel experiences a structural failure, allowing observers to catalog the failure point of flywheels constructed from one or more particular materials.

However, conventional methods of testing cylindrical structures such as those described above suffer from several undesirable collateral consequences.

In particular, since testing is designed to accomplish structural failure of the test material by spinning at high speeds, it is common for the flywheel to experience a sudden, total structural failure, where the flywheel is accordingly disengaged from the central axis of rotation and ejected at extremely high velocity away from said axis. Indeed, this complication is the precise reason that conventional testing is typically conducted remotely—the ejected pieces of the test structure possess extremely high kinetic energy and cause devastating damage to the test facility (as well as anything inside the test facility).

Moreover, constructing remote test facilities, and reconstructing such facilities (or constructing new ones) after experiencing such a catastrophic failure is a complex, time-consuming, and expensive undertaking. All these collateral consequences undesirably impact the efficiency of the overall construction and testing process for new structural configurations and/or material compositions for cylindrical structures.

Accordingly, it would be desirable to provide systems and methods for testing the internal pressure load capacity of cylindrical structures without using high-velocity spinning as a mechanism for generating a failure event. These developments would improve the efficiency of the testing process, reducing both the time and cost of testing procedures by obviating the need to construct or reconstruct testing facilities after catastrophic failure and corresponding collateral damage. Furthermore, by avoiding the spin-to-fail test approach, the dangers presented thereby may be avoided, obviating the need for remote testing facilities.

SUMMARY

In one embodiment, an apparatus, includes: a mandrel; an expansion cylinder, comprising: opposite first and second ends; an inner circumferential surface extending between the ends and characterized by an inner diameter, the inner circumferential surface defining a hollow cavity; an outer circumferential surface extending between the ends and characterized by an outer diameter that is greater than the inner diameter; and a plurality of slots extending from the inner circumferential surface to the outer circumferential surface and latitudinally oriented between the ends; and one or more base plates configured to engage one of the ends of the expansion cylinder, wherein the mandrel is physically configured to engage the expansion cylinder along the inner circumferential surface thereof for causing expansion thereof.

In another embodiment, a method includes: arranging an expansion cylinder inside a test cylinder; arranging a mandrel inside the expansion cylinder; applying a force to the mandrel for exerting a radial force on the expansion cylinder; and detecting one or more indicia of a structural failure of the test cylinder.

Other aspects and embodiments of the present invention will become apparent from the following detailed description, which, when taken in conjunction with the drawings, illustrate by way of example the principles of the invention.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations as would be understood by the skilled artisan reading the present descriptions.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

Except where otherwise defined, the terms "about" and "approximately" with reference to a value indicate that value up to ±10% of the value.

In one general embodiment, an apparatus includes: a mandrel; an expansion cylinder having: opposite first and second ends, an inner circumferential surface extending between the ends and characterized by an inner diameter, the inner circumferential surface defining a hollow cavity, an outer circumferential surface extending between the ends and characterized by an outer diameter that is greater than the inner diameter; and a plurality of slots extending from the inner circumferential surface to the outer circumferential surface and latitudinally oriented between the ends; and one or more base plates configured to engage one of the ends of the expansion cylinder, where the mandrel is physically configured to engage the expansion cylinder along the inner circumferential surface thereof for causing expansion thereof.

In another general embodiment, a method includes: arranging an expansion cylinder inside a test cylinder; arranging a mandrel inside the expansion cylinder; applying a force to the mandrel for exerting a radial force on the expansion cylinder; and detecting one or more indicia of a structural failure of the test cylinder.

Figure 1A:
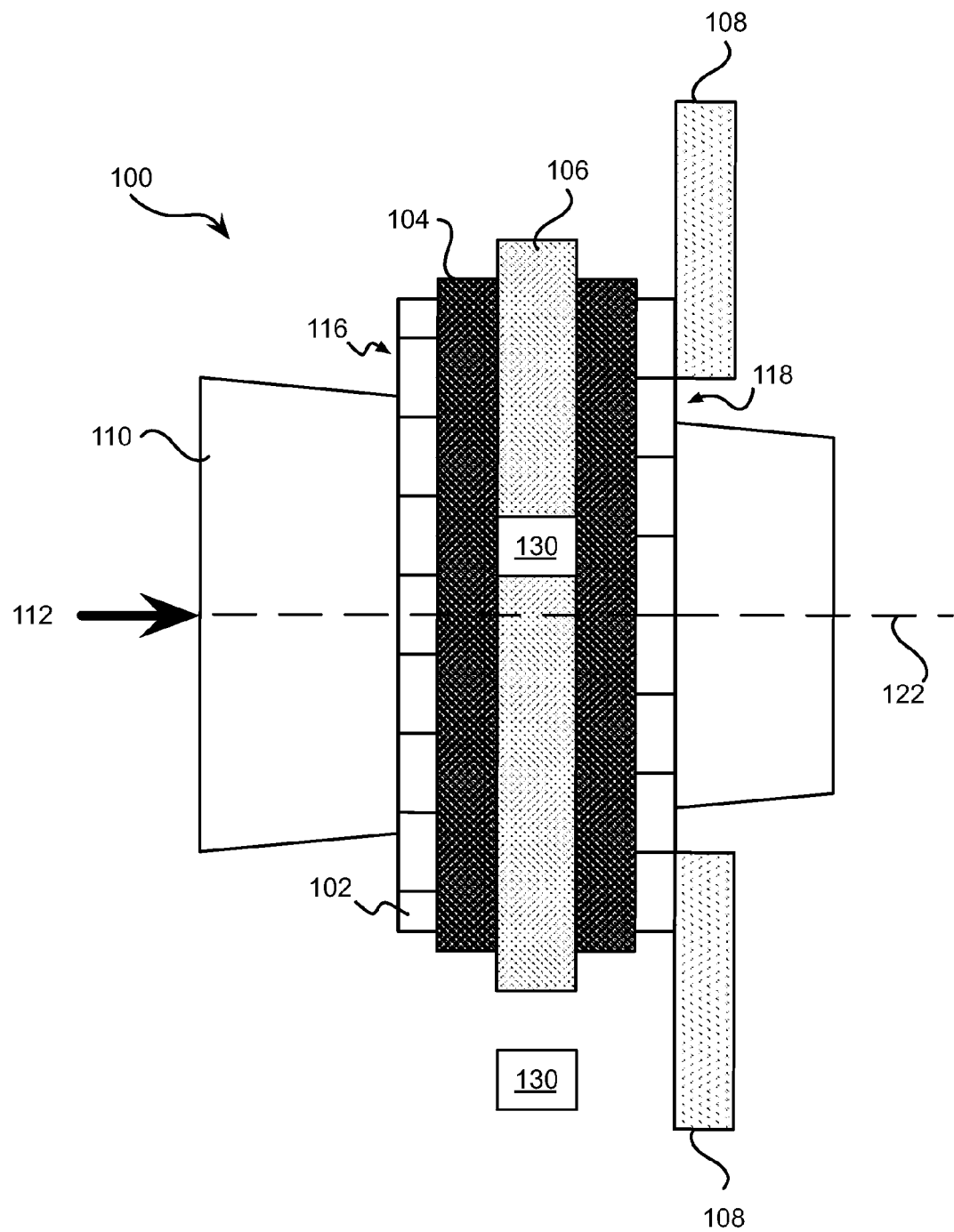
FIG. 1A is a schematic diagram of a system for testing internal pressure load capacity of a cylindrical structure, shown from a side view, according to one embodiment.

Referring to FIG. 1A, which is a schematic diagram of a system 100 for testing internal pressure load capacity of a structure having at least a portion thereof characterized by a substantially cylindrical shape (e.g. test cylinder 106), shown from a side view, according to one embodiment. As shown in the embodiment represented in FIG. 1A, the system includes a mandrel 110 engaging an expansion cylinder 102 along an interior circumferential surface thereof. In some approaches, the mandrel 110 may be physically configured to engage the expansion cylinder along its inner circumferential surface for causing expansion thereof.

In some approaches, the mandrel 110 may be constructed at least in part from a material that is rigid and strong, and in particular may be a machined metal such as steel; titanium; aluminum; steel alloy; titanium alloy; aluminum alloy; etc. as would be understood by one having ordinary skill in the art upon reading the present descriptions.

As shown in FIG. 1A, the system 100 may also include an optional liner 104 positioned on an outside of the outer circumferential surface of the expansion cylinder 102. Advantageously, the liner 104 may facilitate substantially uniform expansion of the expansion cylinder by uniformly distributing radial forces 124 (not shown in FIG. 1A, see FIG. 1B) being applied via the expansion cylinder 102 as the mandrel 110 travels through the hollow cavity 120 (not shown in FIG. 1A, see FIG. 1H) of the expansion cylinder 102 along a central axis 122 thereof upon application of a force 112 to the mandrel.

In some approaches, the liner 104 may be constructed at least in part from a material that is ductile and strong, such as steel; titanium; aluminum; steel alloy; titanium alloy; aluminum alloy; etc. as would be understood by one having ordinary skill in the art upon reading the present descriptions.

With continuing reference to FIG. 1A, the system 100 includes a test cylinder 106 positioned surrounding the outer circumferential surface of the liner 104. In operation, as will be discussed in more detail below with reference to FIG. 2 and method 200, radial forces 124 (not shown in FIG. 1A, see FIG. 1B) are applied to the test cylinder 106 via the expansion cylinder 102 and the liner 104 as the mandrel 110 travels through the hollow cavity 120 (not shown in FIG. 1A, see FIG. 1F) of the expansion cylinder 102 along a central axis 122 thereof upon application of a force 112 to the mandrel. In this manner, it is possible to test the structural integrity of the test cylinder 106.

As additionally shown in FIG. 1A, the system 100 further includes one or more base plates 108 configured to engage one of the ends of the expansion cylinder 102. In operation, the base plates provide a structural platform against which the expansion cylinder 102 may be stabilized for expansion as the mandrel 110 travels through the hollow cavity 120 (not shown in FIG. 1A, see FIG. 1F) of the expansion cylinder 102 along a central axis 122 thereof upon application of a force 112 to the mandrel 110. As shown in FIG. 1A, applying the force 112 to the mandrel 110 urges the mandrel 110 to travel through the expansion cylinder 102 in an x-direction, according to the exemplary dimensions indicated in FIG. 1A.

Figure 1B:
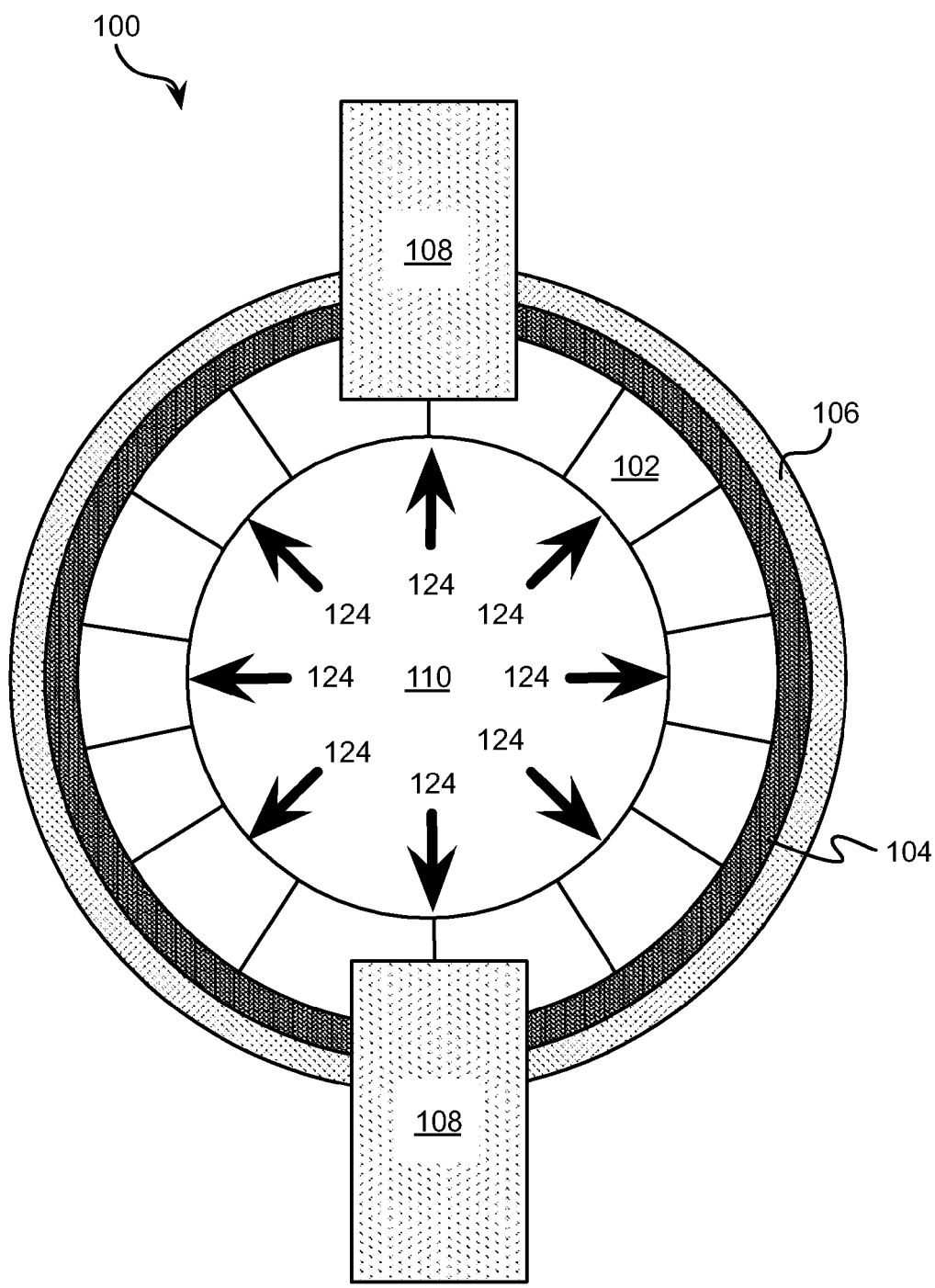
FIG. 1B is a schematic diagram of a system for testing internal pressure load capacity of a cylindrical structure, shown from a front view (i.e. rotated 90° to the right from the view shown in FIG. 1A), according to one embodiment.
Figure 1C:
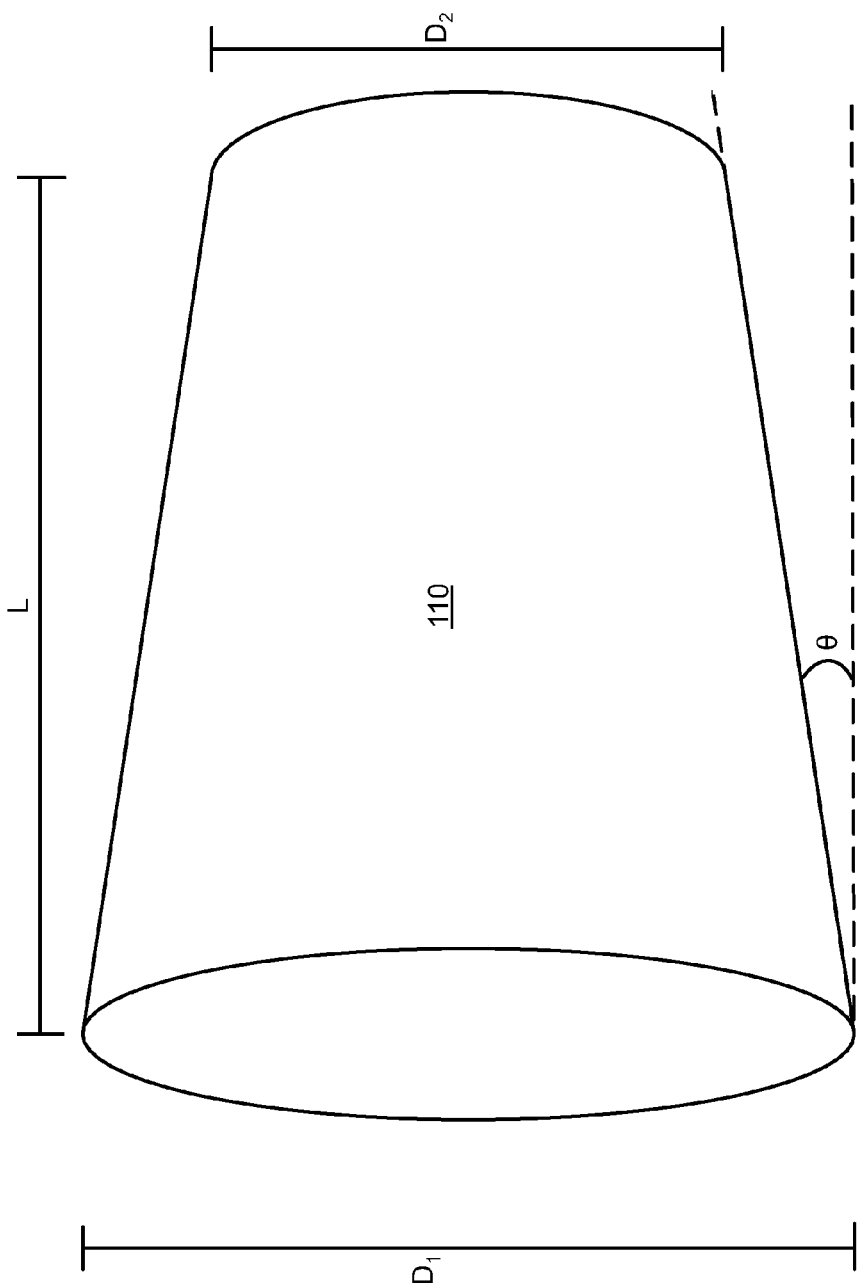
FIG. 1C depicts a mandrel having a periphery characterized by a substantially conical shape and a taper angle $\theta$, according to one embodiment.
Figure 1F:
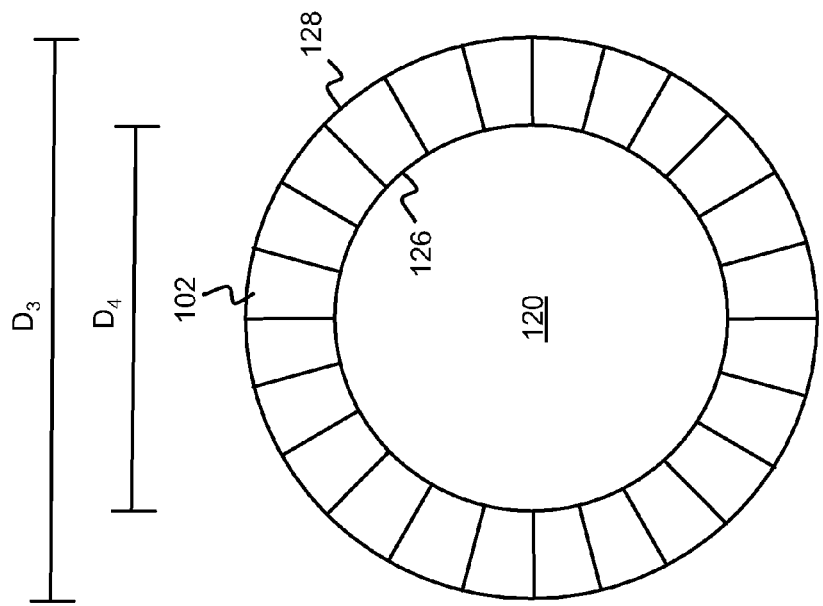
FIG. 1F depicts a cross-sectional view of an expansion cylinder shown from a front view (i.e. rotated 90° to the right from the view shown in FIGS. 1D and 1E) in a compact configuration before expansion, according to one embodiment.
Figure 1E:
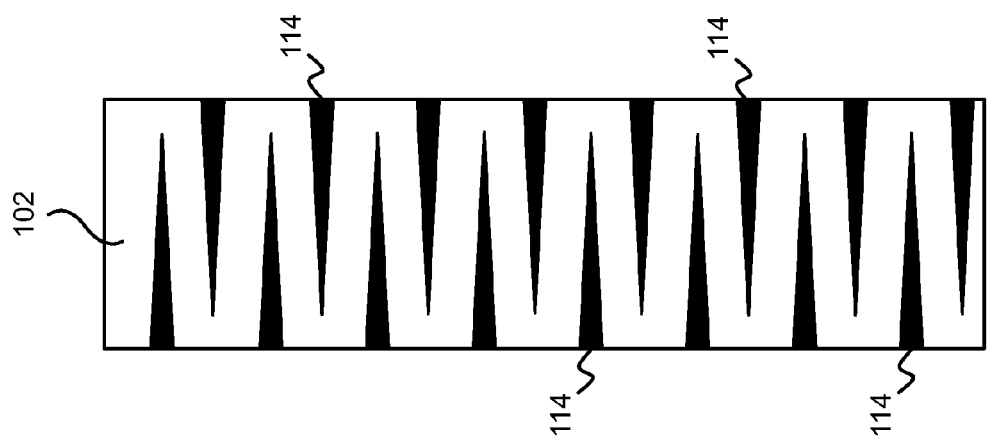
FIG. 1E is a schematic representation of an expansion cylinder in an extended configuration after expansion, shown from a side view according to one embodiment.
Figure 1D:
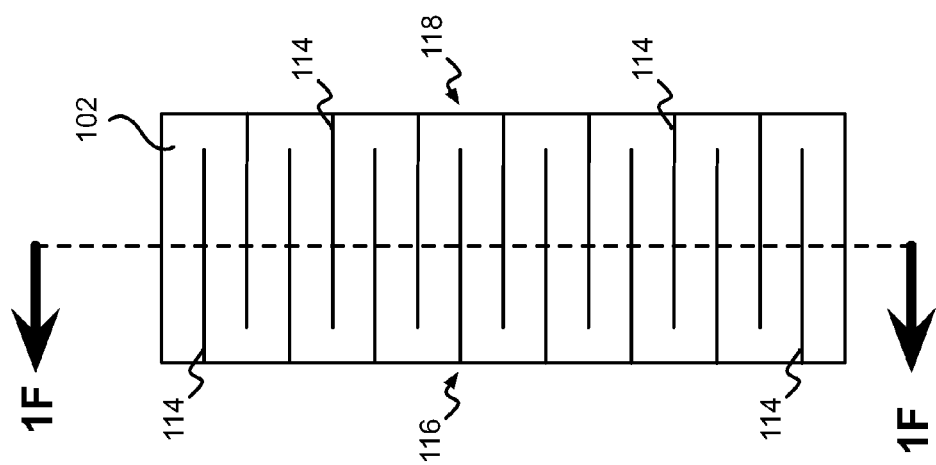
FIG. 1D is a schematic representation of an expansion cylinder in a compact configuration before expansion, shown from a side view according to one embodiment.

In one embodiment, with reference to FIGS. 1D-1F the expansion cylinder 102 includes opposite first and second ends 116, 118; an inner circumferential surface 126 extending between the ends 116, 118 and characterized by an inner diameter, the inner circumferential surface 126 defining a hollow cavity 120; an outer circumferential surface 128 extending between the ends 116, 118 and characterized by an outer diameter that is greater than the inner diameter; and a plurality of slots 114 extending from the inner circumferential surface to the outer circumferential surface 128 and oriented in a latitudinal direction of the expansion cylinder 102 between the ends.

In several embodiments, and with reference again to FIG. 1A, the system 100 may also include one or more sensors 130 configured to detect one or more indicia of a structural failure of a test cylinder 106. Furthermore, sensors 130 may be arranged and/or positioned in any suitable location or configuration enabling the sensors 130 to detect the one or more indicia of structural failure of the test cylinder 106. For example, the sensors 130 may include foil gages arranged around an exterior circumferential surface of the test cylinder and configured for detecting an amount of strain placed on the test cylinder 106, detecting an amount of expansion of the inner and/or outer diameter of the test cylinder 106, etc. as would be understood by one having ordinary skill in the art upon reading the present descriptions.

As will be appreciated by one having ordinary skill in the art upon reading the present descriptions, any suitable measure for determining a structural failure of a test cylinder 106 may be detected using an appropriate sensor, in various approaches. In several exemplary embodiments, the one or more indicia of the structural failure may include one or more of: a rapid decrease in an amount of force required to move the mandrel 110 through the hollow cavity; an amount of strain exerted on the test cylinder 106; an increase in one or more of the inner diameter of the test cylinder 106 and the outer diameter of the test cylinder 106; and a displacement of the mandrel 110.

Referring now to FIG. 1B, which is a schematic diagram of a system 100 for testing internal pressure load capacity of a cylindrical structure, shown from a front view (i.e. rotated 90° to the left from the view shown in FIG. 1A), according to one embodiment. Thus, upon reading the present descriptions, one having ordinary skill in the art will appreciate that the perspective of the inventive embodiment depicted in FIG. 1B is from a position to the right of the system 100 as shown in FIG. 1A, and facing the system 100 such that the mandrel 110 would be urged to move toward the observer upon application of the force 112 thereto.

As may be seen in FIG. 1B, from the perspective shown therein the system 100 represents a concentric ring structure according to one embodiment having two base plates 108 imposed between the observer and the concentric ring structure. While FIG. 1B shows the base plates 108 positioned near the top and bottom of the concentric ring structure, respectively, one having ordinary skill in the art will appreciate that any location for the base plates 108 may be employed so long as said base plates 108 are capable of engaging the expansion cylinder 102 and stabilizing said expansion cylinder 102 such that portions of the expansion cylinder 102 engaging the base plates 108 do not move laterally with the mandrel 110 as the force 112 is applied to the mandrel 110, urging the mandrel 110 to move through the expansion cylinder 102.

As will be appreciated by one having ordinary skill in the art from viewing FIG. 1B in light of the present descriptions, the inventive embodiment depicted in FIG. 1B substantially represents a concentric ring structure, where the central portion of the structure is occupied by the mandrel 110, said mandrel 110 being interior to the expansion cylinder 102 around at least a portion of the exterior circumferential surface of the mandrel 110. Similarly, expansion cylinder 102 is wrapped by a liner 104 around at least a portion of the exterior circumferential surface of the expansion cylinder 102. Finally, the outermost region of the concentric ring structure as depicted in FIG. 1B is occupied by the test cylinder 106, which is wrapped around at least a portion of the exterior circumferential surface of the liner 104, in one embodiment.

During operation, as the mandrel 110 moves through the central portion of the expansion cylinder 102, outward radial forces 124 are applied to the expansion cylinder 102, causing expansion thereof. In preferred embodiments, the outward radial forces 124 are applied uniformly to the interior circumferential surface 126 of the expansion cylinder 102, causing substantially uniform expansion thereof.

As discussed above regarding FIG. 1A, some embodiments within the scope of the present disclosures may omit the liner 104, in which case the test cylinder 106 would occupy the position of the liner 104 as shown in FIG. 1B, i.e. the test cylinder 106 would be wrapped around the exterior circumferential surface of the expansion cylinder 102.

Thus, according to some embodiments the test cylinder 106 includes an inner circumferential surface characterized by an inner diameter and an outer circumferential surface characterized by an outer diameter. Moreover, the inner diameter of the test cylinder 106 is greater than or equal to the outer diameter of the expansion cylinder 102.

Now concerning mandrel 110 in detail, FIG. 1C depicts a mandrel 110 having a periphery characterized by a substantially conical shape and a taper angle $\theta$, according to one embodiment. In various approaches $\theta$ is an angle having a value in a range from about 0° to about 25°, and in particularly preferred embodiments $\theta$ is about 5°.

Moreover, in the embodiment depicted in FIG. 1C the mandrel 110 is characterized by a length L, an upper diameter $D_1$ and a lower diameter $D_2$. As will be appreciated by one having ordinary skill in the art reading the present descriptions, since the mandrel 110 is characterized by a substantially conical shape, the upper and lower diameters thereof exhibit a relationship such that $D_1 > D_2$. While the configuration depicted in FIG. 1C shows a frustoconical configuration (i.e. a substantially conical outer periphery where the tip of the cone is truncated to form a more cylindrical shape) for mandrel 110, skilled artisans will appreciate that other configurations are also within the scope of the present disclosures, including, e.g. true conical (i.e. $D_2 = 0$), pyramidal (the pyramid base being a triangle, square, rectangle, octagon, etc.), frustopyramidal, or any other suitable shape as would be appreciated by a skilled artisan reading the present descriptions. The only limitation on the configuration of mandrel 110 is that it should be capable of engaging the inner surface of the expansion cylinder 102. Thus, if expansion cylinder 102 is not truly cylindrical, or even if cylindrical has an inner surface characterized by a shape other than a circular configuration (e.g. square, rectangular, triangular, etc.) then the mandrel 110 may accordingly have a compatible shape so as to effectively engage the expansion cylinder 102 along the inner surface thereof, in various embodiments.

In preferred embodiments, one advantageous consequence of having a mandrel 110 and expansion cylinder 102 with highly similar configurations is to facilitate substantially uniform application of radial forces to the entire inner surface of the expansion cylinder 102 as the mandrel 110 passes through the hollow cavity 120 thereof. In operation, this results in substantially uniform expansion of the expansion cylinder 102, ensuring that the stress test being performed on the test cylinder 106 is a highly accurate representation of the overall structural integrity thereof, as opposed to only a particular region as would be the case for nonuniform application of force(s) to the expansion cylinder 102 (e.g. applying force to a single point or subset of points taken from all possible points along the inner surface of the expansion cylinder 102.

Regarding the expansion cylinder 102 in particular, FIG. 1D is a schematic representation of an expansion cylinder 102 in a compact configuration before expansion, shown from a side view according to one embodiment. As can be seen in FIG. 1D, the expansion cylinder 102 includes opposite ends 116, 118 and a plurality of slots 114 extending between the opposite ends 116, 118 in a latitudinal direction of the expansion cylinder 102. In some embodiments, the slots 114 may extend from opposite ends 116, 118 in an alternating fashion so as to form a substantially serpentine pattern of expansion cylinder 102 material, as depicted in FIGS. 1D and 1E. Furthermore, slots 114 may extend fully through the depth of the expansion cylinder 102, i.e. slots 114 extend from the inner circumferential surface of the expansion cylinder 102 all the way to the outer circumferential surface of the expansion cylinder 102, as shown more clearly in FIG. 1F. In more embodiments the slots 114 may extend from one of the opposite ends 116, 118, but not completely extend to the other of the opposite ends 116, 118, again as shown in FIGS. 1D and 1E.

While the slots 114 may be substantially linear, and moreover substantially straight, as shown according to the inventive embodiments depicted in FIGS. 1D and 1E, the scope of the present disclosures is not so limited. Other embodiments within the scope of the present disclosure may employ slots characterized by a curved line, a zigzag pattern (e.g. 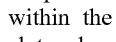), an expanding web (e.g. XXXXXX, see also FIG. 1I for a depiction of a compact configuration of an expanding web slot pattern prior to expansion) etc. as would be appreciated by one having ordinary skill in the art upon reading the present descriptions.

In operation, the slots 114 of expansion cylinder 102 facilitate substantially uniform expansion of the expansion cylinder 102 as the mandrel 110 passes through the hollow cavity 120 thereof. FIGS. 1D and 1E depict the expansion cylinder before and after such expansion, respectively, in one embodiment. As can be seen, during expansion the slots 114 may expand along a longitudinal direction of the expansion cylinder 102 as the expansion cylinder 102 expands, as measured by an inner diameter $D_3$ and/or an outer diameter $D_4$ thereof, in some embodiments.

In some approaches, the expansion cylinder 102 may include one or more materials such as steel; titanium; aluminum; steel alloys; titanium alloys aluminum alloys, etc. as would be understood by one having ordinary skill in the art upon reading the present descriptions.

FIG. 1F depicts a cross-sectional view of an expansion cylinder 102 shown from a front view (i.e. rotated 90° to the right from the view shown in FIGS. 1D and 1E) in a compact configuration before expansion, according to one embodiment. The cross-sectional view depicted in FIG. 1F is a longitudinal section taken from approximately a latitudinal midpoint of the expansion cylinder 102. From this view, it is apparent that the slots 114 extend from the inner circumferential surface of the expansion cylinder 102 all the way to the outer circumferential surface of the expansion cylinder 102, in some approaches.

According to one embodiment, the hollow cavity 120 of expansion cylinder 102 may also be seen in FIG. 1F, where said hollow cavity 120 is defined by the inner circumferential surface of the expansion cylinder 102. Thus, expansion cylinder 102 is characterized by an outer diameter $D_3$ and an inner diameter $D_4$, where the inner diameter of expansion cylinder 102 corresponds to the diameter of the hollow cavity 120 in a given cross sectional slice of expansion cylinder 102.

Skilled artisans reading the present descriptions will appreciate that various embodiments of the inventive system may employ expansion cylinders 102 having an inner circumferential surface that may or may not be characterized by a taper angle ϕ (not shown). Where an expansion cylinder 102 having an inner circumferential surface characterized by a taper angle ϕ is employed, the inner diameter $D_4$ of expansion cylinder 102 will vary from cross-section to cross-section, preferably in a linear fashion. Thus, in one embodiment, the inner diameter $D_4$ of expansion cylinder 102 nearest a point-of-entry of mandrel 110 (e.g. the left side of the expansion cylinder 102 as depicted in FIGS. 1A-1B, 1D-1E and 1G-1H) may be greater than the inner diameter $D_4$ of expansion cylinder 102 nearest a point-of-exit of mandrel 110 (e.g. the right side of the expansion cylinder 102 as depicted in FIGS. 1A-1B, 1D-1E and 1G-1H), in some embodiments.

In particularly preferred embodiments, the taper angle ϕ of the inner circumferential surface of expansion cylinder 102 may be substantially or completely identical to the taper angle θ of the outer periphery of mandrel 110. Systems employing a mandrel 110 and an expansion cylinder 102 having substantially similar or equal taper angles θ and ϕ, respectively, are preferable because such configurations greatly facilitate the uniform application of radial forces 124 to the test cylinder 106 via expansion cylinder 102 and/or liner 104. Of course, as will be appreciated by skilled artisans upon reading the present descriptions, other configurations where θ≠ϕ are also within the scope of the present descriptions, as well as configurations where the expansion cylinder 102 exhibits no taper along the inner circumferential surface thereof (i.e. ϕ=0).

Figure 1H:
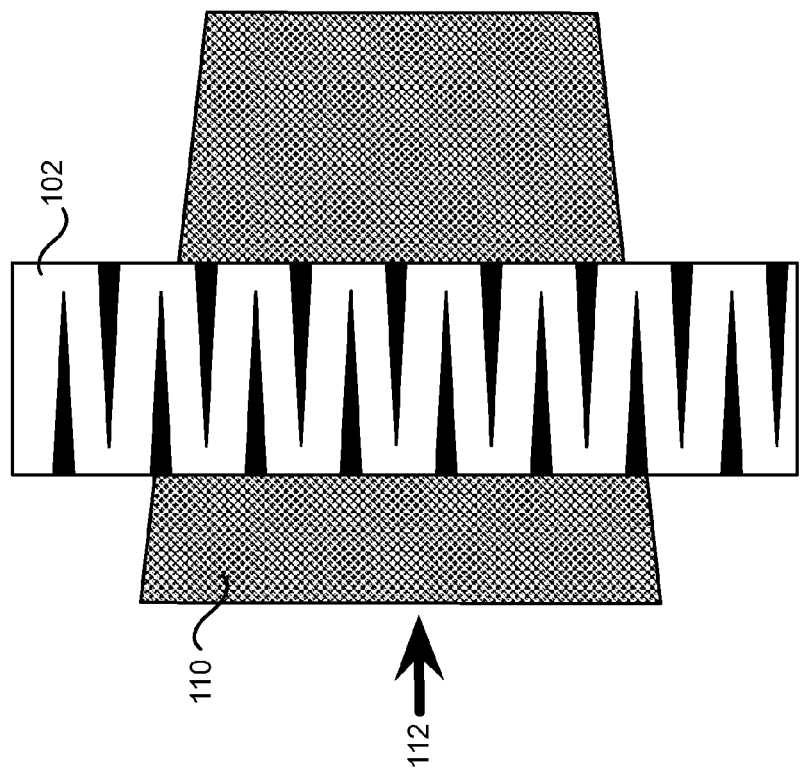
FIG. 1H is a schematic representation of an expansion cylinder engaged by a mandrel in an expanded configuration after expanding as a result of applied radial forces, shown from a side view according to one embodiment.
Figure 1G:
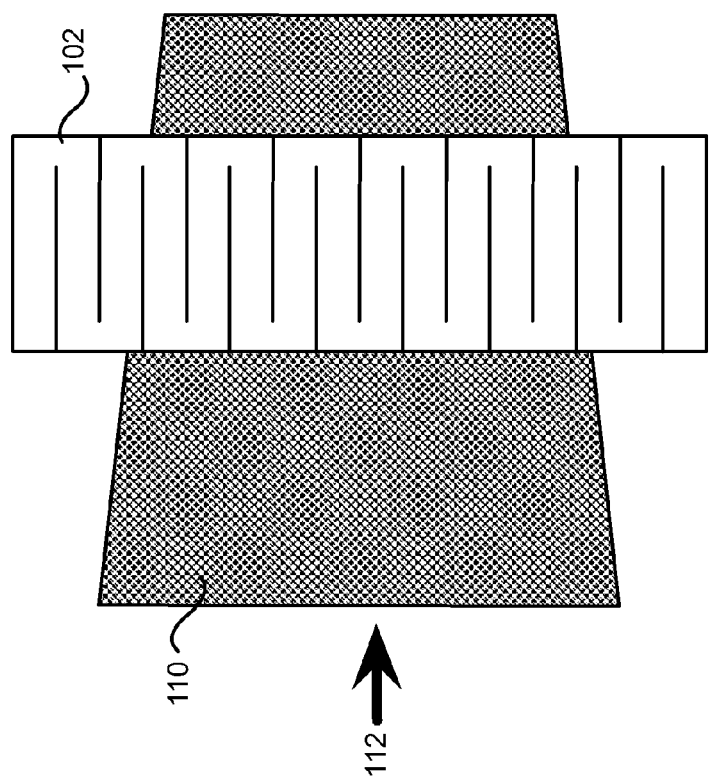
FIG. 1G is a schematic representation of an expansion cylinder engaged by a mandrel in a compact configuration before expansion, shown from a side view according to one embodiment.
Figure 1I:
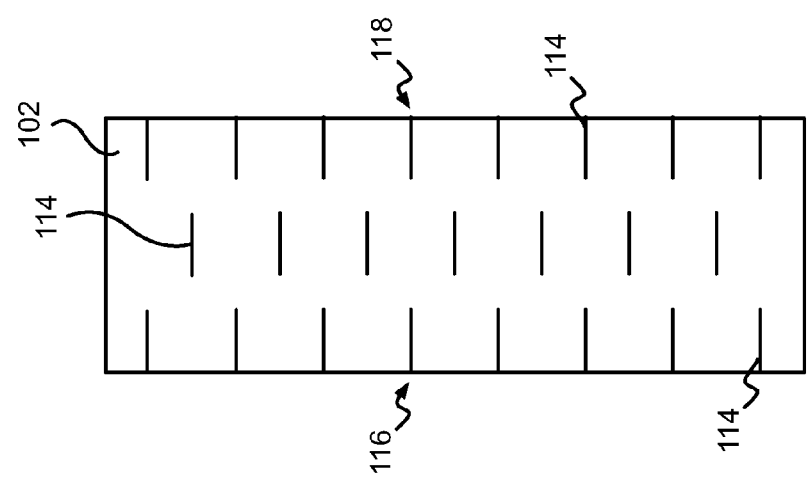
FIG. 1I is a schematic representation of an expansion cylinder engaged by a mandrel in a compact configuration before expansion, shown from a side view according to one embodiment.

With reference to FIGS. 1G and 1H, the mechanism for expanding expansion cylinder 102 by pushing mandrel 110 through the hollow cavity thereof will be described. FIG. 1G is a schematic representation of an expansion cylinder 102 engaged by a mandrel 110 in a compact configuration before expansion, shown from a side view according to one embodiment; and FIG. 1H is a schematic representation of an expansion cylinder 102 engaged by a mandrel 110 in an expanded configuration after expanding as a result of applied radial forces, shown from a side view according to one embodiment.

As can be seen in FIGS. 1G and 1H, as the mandrel travels through the hollow cavity of expansion cylinder 102, the outer peripheral surface of mandrel 110 contacts the inner circumferential surface of expansion cylinder 102, and subsequently exerts radial forces on the inner circumferential surface of expansion cylinder 102 in an outward direction. As the radial forces increase to a point where the outward force exceeds an elastic strength threshold of the expansion cylinder 102 material, the expansion cylinder 102 expands as measured by one or more of an outer diameter $D_3$ and an inner diameter $D_4$, in some approaches. Moreover, this expansion is preferably substantially uniform, as facilitated by the expansion of slots 114 along a longitudinal direction of the expansion cylinder 102.

In operation, according to one embodiment a liner 104 and/or test cylinder 106 may surround the expansion cylinder 102, as described above with reference to FIG. 1B. Outward radial forces 124 may be transferred from the expansion cylinder 102 to the test cylinder 106 via optional liner 104 so as to exert a strain on the test cylinder 106. In preferred approaches, the mandrel 110 may be pushed, pulled, or otherwise moved through the hollow cavity of expansion cylinder 102 and the force applied to test cylinder 106 may be monitored. Outward radial forces 124 may be increased in magnitude until the test cylinder 106 experiences a structural failure, thereby providing an accurate estimate of the structural integrity of the test cylinder 106 material and/or configuration, in various embodiments.

According to the presently described systems, stress testing may further include detecting the structural failure discussed immediately above, in some approaches. Specifically, structural failure may be detected using sensors as described above, and said sensors may operatively detect one or more indicia of a structural failure of the test cylinder 106, e.g. a rapid decrease in an amount of force required to push the mandrel through the hollow cavity; an amount of strain exerted on the test cylinder; an increase in one or more of the inner diameter of the test cylinder and the outer diameter of the test cylinder; a displacement of the mandrel, etc. as would be understood by one having ordinary skill in the art upon reading the present descriptions. In one embodiment, structural failure of the test cylinder may be indicated by an increase in one or more of the inner diameter of the test cylinder 106 and the outer diameter of the test cylinder 106 of about 1.5% to about 2% (e.g. by length).

Moreover, in some embodiments the system 100 described herein may include a mechanism coupled to the mandrel 110 and configured to apply a force 112 to the mandrel 110 in a direction parallel to the central axis 122 of the expansion cylinder 102, as shown particularly in FIGS. 1A and 1G-1H. As will be appreciated by one having ordinary skill in the art upon reading the present descriptions, any suitable mechanism for applying the force 112 may be employed, and the force may take any suitable form, such as a pneumatic force, a gravimetric force, a magnetic force, an electrostatic force, etc. as would be appreciated by one having ordinary skill in the art upon reading the present descriptions.

In more configurations, the mandrel 110 may have applied thereto a lubricant, such as a dry lubricant or a wet lubricant, etc., in order to reduce the frictional forces resulting from contact between the mandrel 110 and the inner circumferential surface of expansion cylinder 102. Reducing frictional forces advantageously facilitates smooth movement of the mandrel 110 through the hollow cavity of expansion cylinder 102, reducing the likelihood of a rapid jump in movement that may complicate or render untrustworthy structural failure data collected during a stress test. In addition, applying the lubricant may facilitate uniformity of radial forces applied to the expansion cylinder 102.

Figure 2:
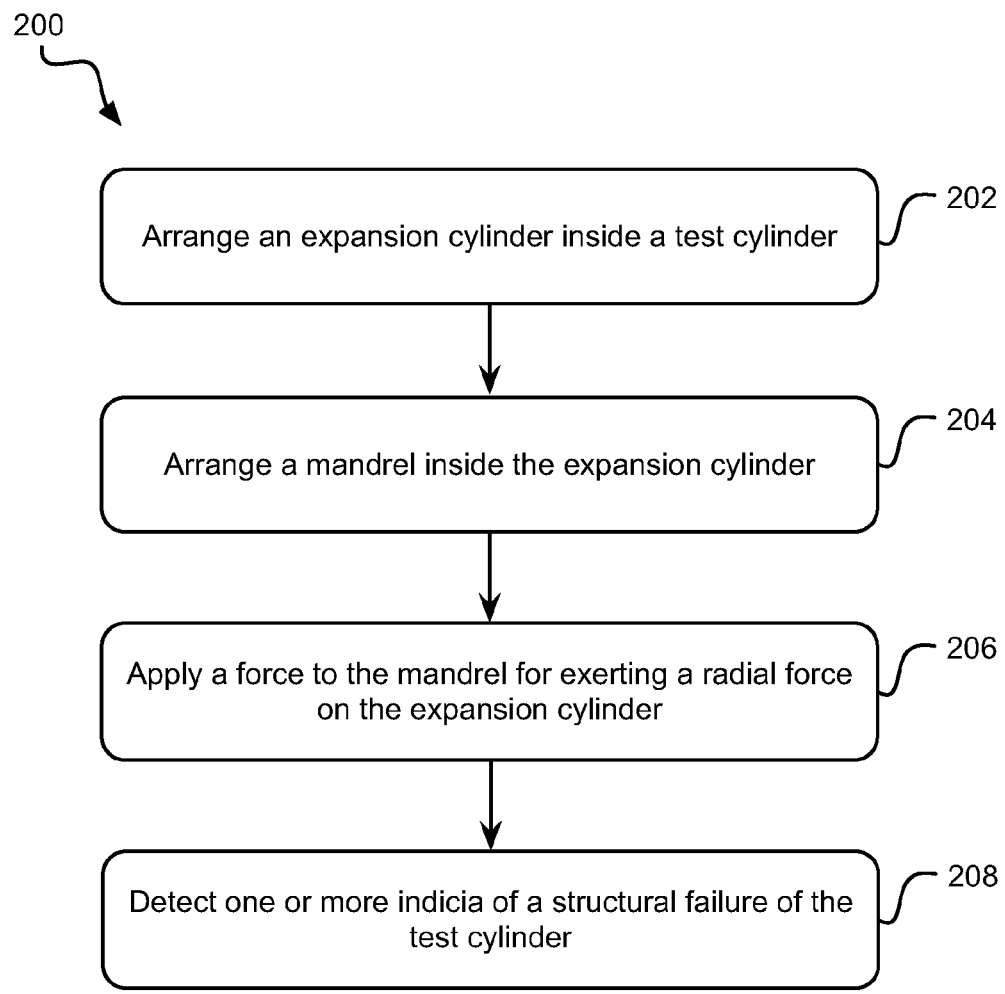
FIG. 2 is a flowchart of a method, according to one embodiment.

FIG. 2 is a flowchart of a method 200, according to one embodiment. As will be appreciated by skilled artisans reading the present descriptions, method 200 may be performed in any suitable environment, including those depicted in FIGS. 1A-1H, among others.

As shown in FIG. 2, method 200 includes operation 202, where an expansion cylinder is arranged inside a test cylinder.

In operation 204, a mandrel is arranged inside the expansion cylinder, preferably in a hollow cavity thereof.

In operation 206, a force is applied to the mandrel in a direction substantially parallel to a central axis of the expansion cylinder.

In operation 208, one or more indicia of a structural failure of the test cylinder 106 are detected. The indicia of structural failure may be as described above, in various approaches.

In addition to operations 202-208 as described above, method 200 may also include additional and/or alternative operations, in several embodiments. For example, in one embodiment, method 200 may include positioning a liner on an outside of an outer circumferential surface of the expansion cylinder; and/or positioning one or more sensors configured to detect the one or more indicia of the structural failure along an outer circumferential surface of the test cylinder.

In one embodiment, strains in the test cylinder may be measured on the outer or lateral surfaces thereof, e.g. using sensors as described herein such as foil gages or some other displacement measuring device. In more embodiments, the motion of loading segments (e.g. mandrel, expansion cylinder, liner, etc.) could also be measured independently.

In some approaches, pressure loads may be determined by calibrating the force magnification through the mandrel by testing materials of known mechanical properties. A sacrificial thin metal liner (e.g., steel or titanium) may also be used between the loading segments and the inner diameter of the composite ring to minimize the stress concentrations at the inner surface of the composite arising from the gaps which may open between segments during expansion. The loading segments may be used in order to apply only radial forces against the inner diameter of the composite ring.

While the expansion of the test cylinder may also be accomplished by forcing the test cylinder directly onto a solid conical wedge, this method may generate both through-thickness compression and shear stresses, which could undesirably lead to premature failure.

Uses and Applications

Illustrative applications of various embodiments include use stress-testing systems and methods for evaluating structural integrity of cylindrical structures such as firearm barrels, flywheels, high-pressure storage vessels, piping, tubing, etc. as would be understood by the skilled artisan upon reading the present descriptions.

Advantageously, the presently disclosed methods permit investigation into structural properties of materials for use in applications described above, among others, without requiring a full-scale test such as flywheel spinning, pressure vessel bursting, or gun firing, etc. Moreover, the presently disclosed systems and methods may be utilized to perform a test on representative subcomponents of a test structure, rather than requiring the entire structure be tested.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. An apparatus, comprising:
a mandrel;
an expansion cylinder, comprising:
  opposite first and second ends;
  an inner circumferential surface extending between the ends and characterized by an inner diameter, the inner circumferential surface defining a hollow cavity;
  an outer circumferential surface extending between the ends and characterized by an outer diameter that is greater than the inner diameter;
  a plurality of slots extending from the inner circumferential surface to the outer circumferential surface and latitudinally oriented between the ends, wherein the slots are characterized by an arrangement selected from:
    a plurality of curved lines;
    a zigzag pattern; and
    an expanding web; and
one or more base plates configured to engage one of the ends of the expansion cylinder; and
one or more sensors,
wherein the one or more sensors are configured to detect one or more indicia of a structural failure of a test cylinder,
wherein at least one of the one or more sensors is configured for positioning along the outer circumferential surface of the test cylinder, and
wherein the mandrel is physically configured to engage the expansion cylinder along the inner circumferential surface thereof for causing expansion thereof.

2. The apparatus as recited in claim 1, further comprising a test cylinder, the test cylinder comprising:
an inner circumferential surface characterized by an inner diameter; and
an outer circumferential surface characterized by an outer diameter;

wherein the inner diameter of the test cylinder is greater than the outer diameter of the expansion cylinder, and wherein the expansion cylinder is positioned inside the inner circumferential surface of the test cylinder.

3. The apparatus as recited in claim 1, wherein each of the slots extends from the inner circumferential surface of the expansion cylinder to the outer circumferential surface of the expansion cylinder.

4. The apparatus as recited in claim 1, wherein the expansion cylinder comprises one or more of titanium and a titanium alloy.

5. The apparatus as recited in claim 1, wherein the mandrel has an outer periphery characterized by a substantially conical shape, wherein the mandrel is characterized by a taper angle θ, and wherein θ is a value in a range from about 15° to about 25°.

6. The apparatus as recited in claim 1, wherein each of the slots is configured to expand along a longitudinal direction of the expansion cylinder.

7. The apparatus as recited in claim 1, further comprising a mechanism coupled to the mandrel, the mechanism being configured to apply a force to the mandrel in a direction substantially parallel to a central axis of the expansion cylinder, and wherein the force comprises one or more of a gravimetric force, a magnetic force, and an electrostatic force.

8. The apparatus as recited in claim 1, wherein the mandrel comprises a material selected from a group consisting of: steel; titanium; aluminum; steel alloy; titanium alloy and aluminum alloy.

9. The apparatus as recited in claim 1, wherein the one or more indicia of the structural failure comprise an increase in one or more of the inner diameter of the test cylinder and the outer diameter of the test cylinder.

10. The apparatus as recited in claim 9, wherein the increase in one or more of the inner diameter of the test cylinder and the outer diameter of the test cylinder is in a range from about 1.5% to about 2%.

11. The apparatus as recited in claim 9, the one or more indicia of the structural failure further comprising at least one of:

a rapid decrease in an amount of force required to push the mandrel through the hollow cavity;

an amount of strain exerted on the test cylinder; and a displacement of the mandrel.

12. An apparatus, comprising:
a mandrel;
an expansion cylinder, comprising:
opposite first and second ends;
an inner circumferential surface extending between the ends and characterized by an inner diameter, the inner circumferential surface defining a hollow cavity;
an outer circumferential surface extending between the ends and characterized by an outer diameter that is greater than the inner diameter; and
a plurality of slots extending from the inner circumferential surface to the outer circumferential surface and latitudinally oriented between the ends; and
one or more base plates configured to engage one of the ends of the expansion cylinder; and
a liner configured for positioning on an outside of the outer circumferential surface of the expansion cylinder, and
wherein the mandrel is physically configured to engage the expansion cylinder along the inner circumferential surface thereof for causing expansion thereof.

13. The apparatus as recited in claim 12, wherein the liner comprises a material selected from a group consisting of: steel; titanium; aluminum; steel alloy; titanium alloy and aluminum alloy.

14. A method, comprising:
arranging an expansion cylinder inside a test cylinder;
arranging a mandrel inside the expansion cylinder;
applying a force to the mandrel for exerting a radial force on the expansion cylinder; and
detecting one or more indicia of a structural failure of the test cylinder, wherein the one or more indicia of the structural failure comprise an increase in one or more of an inner diameter of the test cylinder and an outer diameter of the test cylinder.

15. The method as recited in claim 14, wherein the detecting one or more indicia of a structural failure of the test cylinder further comprises one or more of:

detecting a rapid decrease in an amount of force required to push the mandrel through a hollow cavity of the expansion cylinder;

detecting an amount of strain exerted on the test cylinder; and detecting a displacement of the mandrel.

16. The method as recited in claim 14, wherein applying the force to the mandrel urges the mandrel through a hollow cavity in the expansion cylinder along a central axis of the expansion cylinder, and wherein the force comprises one or more of a gravimetric force, a magnetic force, and an electrostatic force.

17. The method as recited in claim 14, further comprising positioning a liner on an outside of an outer circumferential surface of the expansion cylinder, wherein the liner is configured to facilitate a substantially uniform increase in a circumference of the expansion cylinder as the mandrel moves through a hollow cavity thereof.

18. The method as recited in claim 14, further comprising applying a lubricant to the mandrel.

19. The method as recited in claim 14, further comprising: positioning one or more sensors configured to detect the one or more indicia of the structural failure along an outer circumferential surface of the test cylinder.

* * * * *